(12) United States Patent
Gall et al.

(10) Patent No.: US 7,985,222 B2
(45) Date of Patent: Jul. 26, 2011

(54) OSTEOSYNTHETIC IMPLANTS AND METHODS OF USE AND MANUFACTURE

(75) Inventors: Kenneth A. Gall, Denver, CO (US); Jeffrey A. Tyber, Boulder, CO (US); Douglas J. Pacaccio, Alexandria, VA (US)

(73) Assignee: Medshape Solutions, Inc., Atlanta, GA (US)

( * ) Notice: Subject to any disclaimer, the term of this patent is extended or adjusted under 35 U.S.C. 154(b) by 1768 days.

(21) Appl. No.: 11/112,865

(22) Filed: Apr. 21, 2005

(65) Prior Publication Data

US 2005/0240190 A1    Oct. 27, 2005

Related U.S. Application Data

(60) Provisional application No. 60/563,952, filed on Apr. 21, 2004.

(51) Int. Cl.
*A61B 17/58* (2006.01)
*A61F 2/30* (2006.01)

(52) U.S. Cl. ......................................................... 606/60

(58) Field of Classification Search .................. 606/60, 606/62, 63, 300, 301, 308, 320
See application file for complete search history.

(56) References Cited

U.S. PATENT DOCUMENTS

| | | | |
|---|---|---|---|
| 4,452,236 A | 6/1984 | Utsugi ............................. 128/4 |
| 4,665,906 A | 5/1987 | Jervis | |
| 5,067,957 A | 11/1991 | Jervis | |
| 5,120,175 A | 6/1992 | Arbegast et al. | |
| 5,190,546 A | 3/1993 | Jervis | |
| 5,265,456 A | 11/1993 | Kennedy et al. | |
| 5,415,660 A * | 5/1995 | Campbell et al. ............... 606/62 |
| 5,486,183 A | 1/1996 | Middleman et al. | |
| 5,505,734 A | 4/1996 | Caniggia et al. ................ 606/63 |
| 5,597,378 A | 1/1997 | Jervis | |
| 5,601,572 A | 2/1997 | Middleman et al. | |
| 5,632,746 A | 5/1997 | Middleman et al. | |
| 5,720,754 A | 2/1998 | Middleman et al. | |
| 5,749,879 A | 5/1998 | Middleman et al. | |
| 5,820,628 A | 10/1998 | Middleman et al. | |
| 5,904,690 A | 5/1999 | Middleman et al. | |
| 5,964,770 A | 10/1999 | Flomenblit et al. | |
| 6,004,330 A | 12/1999 | Middleman et al. | |

(Continued)

FOREIGN PATENT DOCUMENTS

DE    19708279    9/1998

(Continued)

OTHER PUBLICATIONS

English Translation of WO 2006/120355 (listed above).

(Continued)

*Primary Examiner* — Anu Ramana
(74) *Attorney, Agent, or Firm* — Greenberg Traurig LLP

(57) ABSTRACT

The present invention provides bone fracture fixation devices, systems and methods of use and manufacture. One such bone fixation device includes an elongate element having a responsive zone. The element is adapted to be coupled to the bone so that the responsive zone is positioned adjacent a fracture site in the bone. The responsive zone is adapted to apply a desired pressure to the bone when coupled thereto. In some embodiments, the responsive zone comprises a shape memory material, which may be nickel titanium or Nitinol, to apply compressive pressure across the fracture site for longer periods of time than standard bone screws.

10 Claims, 10 Drawing Sheets

U.S. PATENT DOCUMENTS

| | | | |
|---|---|---|---|
| 6,306,141 | B1 | 10/2001 | Jervis |
| 6,447,523 | B1 | 9/2002 | Middleman et al. |
| 6,451,025 | B1 | 9/2002 | Jervis |
| 6,533,805 | B1 | 3/2003 | Jervis |
| 6,637,995 | B1 | 10/2003 | White |
| 6,688,828 | B1 | 2/2004 | Post |
| 6,986,774 | B2 | 1/2006 | Middleman et al. |
| 7,056,322 | B2 | 6/2006 | Davison et al. |
| 2004/0230193 | A1 | 11/2004 | Cheung et al. |
| 2005/0107791 | A1 | 5/2005 | Manderson ............ 606/62 |

FOREIGN PATENT DOCUMENTS

| | | |
|---|---|---|
| WO | WO95/24870 | 9/1995 |
| WO | WO2005/094705 | 10/2005 |
| WO | WO 2006/120355 | 11/2006 |

OTHER PUBLICATIONS

Ankle Arthrodesis Nail Surgical Technique, Biomet, Inc., Form No. Y-BMT-596R/021500/H, © 2000 Biomet, Inc. Warsaw, IN.

PANTA™ Arthrodesis Nail. Datasheet [online]. Integra LifeSciences Corporation, 2006, [retrieved on Jan. 12, 2007]. Retrieved from the Internet: <http://www.ilstraining.com/Mid%20%20Hindfoot%20Solutions/panta/panta_00.html>.

Retronail Ankle Arthrodesis Arthritic Deformity, Fractures, Failed Fusion. Products [online]. © 2007 orthofix.com, [retrieved on Apr. 4, 2007]. Retrieved from the Internet: <http://www.orthofix.com/products/retronail.asp?cid=5>.

T2™TIBIAL Nailing System. Operative Technique. Stryker, pp. 1-31.

Tibiotalocalcaneal Nailing System Options Made Easy. Surgical Technique. Stryker, 2006. pp. 1-19.

International Search Report, PCT/US06/15207.

El Feninat, Fatiha et al., *Shape Memory Materials for Biomedical Applications*, Advanced Engineering Materials 2002, 4, No. 3, pp. 83, 86, 91-104.

Gall, Ken et al., *Thermomechanics of the shape memory effect in polymers for biomedical applications*, 2005 Wiley Periodicals, Inc., pp. 339-348.

Gall, Ken et al., *Shape-Memory Polymers for Microelectromechanical Systems*, Journal of Microelectromechanical Systems, vol. 13, No. 3, Jun. 2004, pp. 472-483.

Gall, Ken et al., *Shape memory polymer nanocomposites*, ACTA Materialia 50, (2002), pp. 5115-5126.

Jeon, HG et al., *Shape memory and nanostructure in poly(norbornyl-POSS) copolymers*, Polymer International, Polym Int 49 (2000), pp. 453-457.

Langer, Robert et al., *Designing materials for biology and medicine*, Nature, vol. 428, Apr. 1, 2004, pp. 487-492.

Lendlein, Andreas et al., *Light-induced shape-memory polymers*, Nature, vol. 434, Apr. 14, 2005, pp. 879-882.

Lendlein, Andreas et al., *Biodegradable, Elastic Shape-Memory Polymers for Potential Biomedical Applications*, Science, vol. 296, May 31, 2002, pp. 1673-1676.

Lendlein, Andreas et al., *AB-polymer networks based on oligo (ε-caprolactone) segments showing shape-memory properties*, PNAS, Jan. 30, 2001, vol. 98, No. 3, pp. 842-847.

Lin, J. R. et al., *Study on Shape-Memory Behavior of Polyether-Based Polyurethanes. I. Influence of the Hard-Segment Content*, Journal of Applied Polymer Science, vol. 69, (1998), pp. 1563-1574.

Lin, J.R. et al., *Study on Shape-Memory Behavior of Polyether-Based Polyurethanes. II. Influence of Soft-Segment Molecular Weight*, Journal of Applied Polymer Science, vol. 69, (1998), pp. 1575-1586.

Liu, Changdeng et al., *Chemically Cross-Linked Polycyclooctene: Synthesis, Characterization, and Shape Memory Behavior*, Macromolecules, 2002, 35, pp. 9868-9874.

Liu, Yiping et al., *Thermomechanics of shape memory polymers: Uniaxial experiments and constitutive modeling*, International Journal of Plasticity, 22 (2006), pp. 279-313.

Liu, Yiping et al., *Thermomechanical recovery couplings of shape memory polymers in flexure*, Institute of Physics Publishing, Smart Mater. Struct. 12 (2003), pp. 947-954.

Maitland Ph.D., Duncan J. et al., *Photothermal Properties of Shape Memory Polymer Micro-Actuators for Treating Stroke*, Lasers in Surgery and Medicine 30 (2002), pp. 1-11.

Metcalfe, Annick et al., *Cold hibernated elastic memory foams for endovascular interventions*, Biomaterials 24 (2003), pp. 491-497.

Metzger, Melodie F. et al., *Mechanical Properties of Mechanical Actuator for Treating Ischemic Stroke*, Biomedical Microdevices, vol. 4, No. 2, May 2002, pp. 89-96.

Smith, Thor L., *Strength of Elastomers-A Perspective*, Polymer Engineering and Science, vol. 17, No. 3, Mar. 1977, pp. 129-143.

Smith, Thor L., *Ultimate Tensile Properties of Elastomers. I. Characterization by a Time and Temperature Independent Failure Envelope*, Journal of Polymer Science: Part A, vol. 1, No. 12 (1963), pp. 3597-3615.

Smith, Thor L. et al., *Time and Temperature Dependence of the Ultimate Properties of an SBR Rubber at Constant Elongations*, Journal of Applied Physics, vol. 31, No. 11, Nov. 1960, pp. 1892-1898.

Takahashi, Toshisada et al., *Structure and Properties of Shape-Memory Polyurethane Block Copolymers*, Journal of Applied Polymer Science, vol. 60, (1996), pp. 1061-1069.

Tobushi, H. et al., *Thermomechanical Constitutive Modeling in Shape Memory Polymer of Polyurethane Series*, Journal of Intelligent Material Systems and Structures, vol. 8, Aug. 1997, pp. 711-718.

Tobushi, Hisaaki, et al., *Thermomechanical properties in a thin film of shape memory polymer of polyurethane series*, Smart Mater. Struct. 5 (1996), pp. 483-491.

Wache, H.M. et al., *Development of a polymer stent with shape memory effect as a drug delivery system*, Journal of Materials Science: Materials in Medicine 14 (2003), pp. 109-112.

Yahia, L., (Ed.), *Shape Memory Implants*, Springer-Verlag Berlin Heidelberg New York, 2000, (complete book—out of print).

Yakacki, Christopher M. et al., *Strong and Biocompatible Shape Memory Polymers for Soft Tissue Orthopedic Fixation*, Submitted to Nature Materials, 2006, pp. 1-27.

Zhu, G. et al., *Shape-Memory Effects of Radiation Crosslinked Poly(ε-caprolactone)*, Journal of Applied Polymer Science, vol. 90, (2003), pp. 1589-1595.

Andreasen et al., *Laboratory and Clinical Analyses of Nitinol Wire*, American Journal of Orthepedics, vol. 73, No. 2, pp. 142-151 (Feb. 1978).

Cragg et al., *A New Percutaneous Vena Cava Filter*, American Journal of Roentgenology, vol. 141, pp. 601-604 (Sep. 1983).

Wasilewski, R., *Stress-Assisted Martensite Formation in TiNi*, Scripta Metallurgica, vol. 5, No. 2, pp. 127-130 (1971).

Watanabe, K., *Studies on New Superelastic NiTi Orthodontic Wire (Part 1) Tensile and Bend Test*, Dental Material and Devices Magazine, vol. 23, No. 61, pp. 1-61 (1982).

Results of the Partial International Search from corresponding PCT Application No. PCT/US2008/055188.

\* cited by examiner

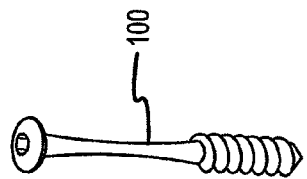
FIG.1A
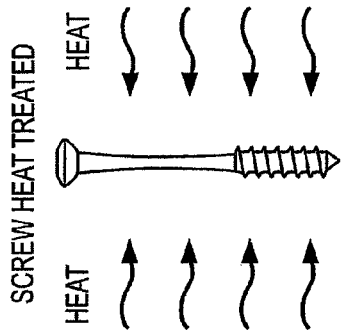
FIG.1C
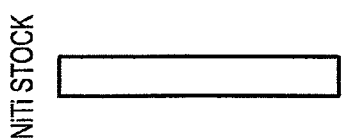
FIG.1B
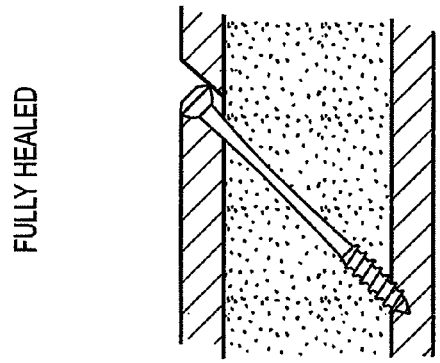
FIG.2C
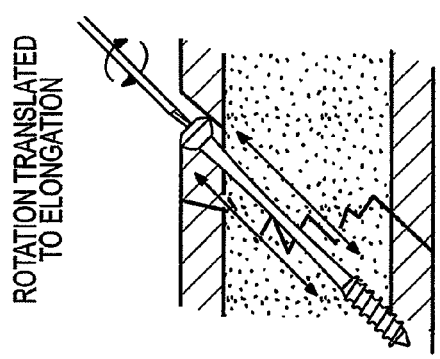
FIG.2B
FIG.2A

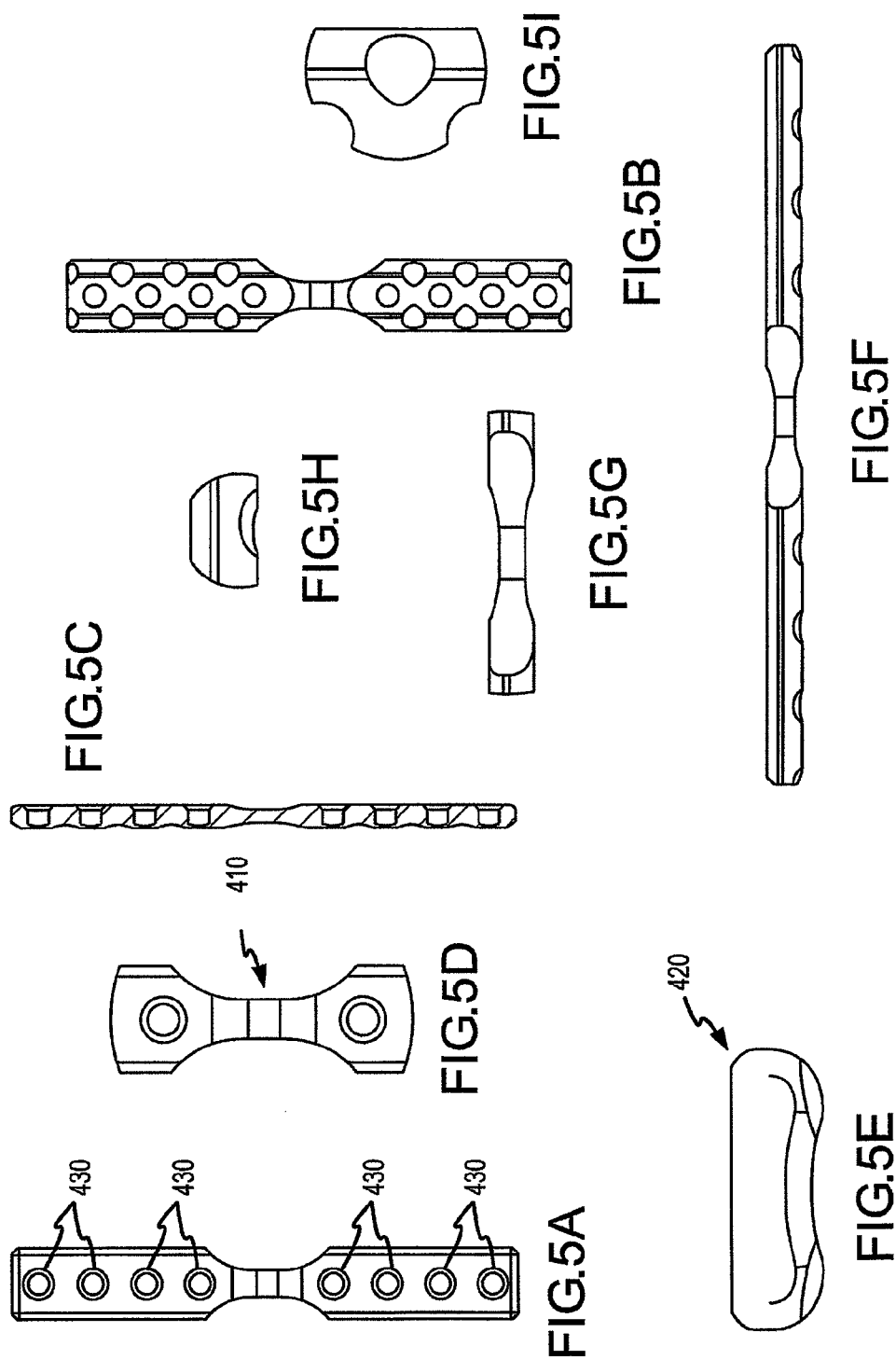

OSTEOSYNTHETIC IMPLANTS AND METHODS OF USE AND MANUFACTURE

CROSS-REFERENCES TO RELATED APPLICATIONS

The present application claims priority to U.S. Provisional Application No. 60/563,952, filed Apr. 21, 2004, entitled Shape Memory Alloy Osteosynthetic Implants, the complete disclosure of which is incorporated herein by reference for all purposes.

BACKGROUND OF THE INVENTION

The present application relates generally to bone fracture repair, and more specifically, to osteosynthetic implants for fracture repair and methods of their use and manufacture.

In 1959, a group of Swiss Orthopedic and General Surgeons formed the Arbeitsgemeinschaft fur Osteosynthesefragen (AO), also known as the Association for the Study of Internal Fixation (ASIF). The AO/ASIF is now a multi-national group of doctors and scientists with the expressed purpose of studying bone healing and continuous development of fracture fixation techniques for patient care. In the United States, as well as most other countries, AO/ASIF guidance regarding skeletal fixation has become the standard of care for traumatic fracture as well as therapeutic osteotomy fixation techniques. It is under these AO/ASIF guidelines that the surgeon plans and carries out procedures to achieve the desired end result of bone healing and skeletal function.

Problems can arise when the bone fracture site is not sufficiently stabilized during the healing timeframe. Depending on the nature of the fracture, screws and plates may be used alone, or in combination. One objective of osteosynthetic implants is the anatomic reduction of the fracture. Another objective would be to minimize or eliminate interfragmentary motion. Still another objective involves increasing or maximizing blood supply to the fracture site by reducing or minimizing additional vascular damage. Excessive interfragmentary motion results in the formation of fibrous, unmineralized scar tissue (resulting in a non-union or pseuo-arthrosis) versus the regeneration of bone. The unmineralized scar tissue is not load supporting and skeletal function is lost. A sufficient blood supply must be maintained to support skeletal metabolism, bone regeneration, and remodeling of the fracture site. The current standard of care includes osteosynthetic devices that are made of either stainless steel or titanium.

The use of stainless steel or titanium in osteosynthetic devices has a long history and reasonable record of success. Over time, however, the stainless steel and titanium fixation constructs (both screws and plates) do not maintain compression across the fracture fragments. The reduction of compression of certain standard material constructs has been observed to be thirty-two percent (32%) over a two week period. As the necrotic surfaces of the fracture are resorbed, a non-load bearing gap develops between the fragments, thereby decreasing compression and increasing the risk of interfragmentary motion and scar tissue formation. Loss of compression is contrary to the objectives of fracture fixation in general, and osteosynthetic implants in particular. Improvements are desired to help maintain compressive load across the fracture site over a longer period of healing.

BRIEF SUMMARY OF THE INVENTION

The present application relates generally to bone fracture repair, and more specifically, to osteosynthetic implants for fracture repair and methods of their use and manufacture. Fracture repair devices, systems and methods include those for repairing intentional fracture sites, such as but not limited to osteotomies, for reconstructive purposes. Bony fusions of surgically resected joints throughout the body are included as well within the scope of the present invention. Fracture fixation devices, systems and methods of the present invention help maintain compressive loads across the fracture site for longer periods of time compared to prior devices. In some embodiments, the use of shape memory materials, including nickel titanium, delivers improved fracture repair characteristics. The present invention further includes methods of use and methods of manufacture of such bone fixation devices and systems.

In one embodiment, a bone fixation device according to the present invention includes an elongate element having a responsive zone. The elongate element is a plate, a nail, or a bone screw in alternative embodiments. The elongate element is adapted to be coupled to the bone so that the responsive zone is positioned adjacent a fracture site in the bone. The responsive zone is adapted to apply a desired pressure to the bone when coupled thereto. In a preferred embodiment, the responsive zone comprises a shape memory material, which may be nickel titanium or Nitinol.

In some embodiments, the elongate element comprises nitinol, while in other aspects, the responsive zone is pseudoelastic at a body temperature. In this manner, the elongate element may be used to apply desired forces at the fracture site. In some embodiments, the responsive zone is generally centrally located in the elongate element. In one aspect, the responsive zone has a smaller overall cross section than a cross section of an end of the elongate element. Such a configuration helps locate the stresses or pressures at a desired location within the elongate element, and more specifically, at the responsive zone.

In some aspects, the bone fixation device further includes a coupler adapted to couple the elongate element to the bone. The coupler may include one or more bone screws, which in some embodiments comprise a shape memory material. In a particular embodiment, the elongate element has first and second end sections each with at least one hole adapted to receive a coupler therethrough to couple the element to the bone. Other embodiments may use two, three, four, or more holes in one or both end sections to fixedly couple the device to the fractured bone.

The present invention further provides bone fixation systems. In one embodiment, the system includes an elongate element having a responsive zone of shape memory material, and a coupler adapted to couple the elongate element to the bone so that the responsive zone is positioned adjacent a fracture site in the bone. In some embodiments, the system includes a removable clamp, with the clamp adapted to maintain the elongate element responsive zone in a desired position prior to coupling of the element to the bone, and may further be adapted to be removed from the elongate element after coupling of the element to the bone. In one aspect, the responsive zone is adapted to apply a desired pressure to the bone when the elongate element is coupled to the bone.

The present invention further provides methods of stabilizing a fractured bone. In one such embodiment, the method includes providing an elongate element, which may be a plate, a bone nail, a bone screw, or related devices. The elongate element has a responsive zone of a shape memory material, with the responsive zone adapted to apply a desired pressure to the bone when coupled thereto. The method includes coupling the elongate element to the bone so that the responsive zone is positioned adjacent a fracture site in the bone.

In one aspect, the method includes applying a force to the elongate element to lengthen the responsive zone a desired amount, maintaining the element in the lengthened position, coupling the element to the bone so that the lengthened responsive zone is positioned adjacent the fracture site, and releasing the elongate element. In some aspects, a clamp is used to maintain the element in the lengthened position. In this manner, the elongate element may be released by removing the clamp. As a result, the stress formed in the responsive zone can be applied to the bone to facilitate fracture site stability, healing, and the like.

In a particular aspect, coupling the elongate element to the bone includes attaching a first coupler to the element and to the bone on a first side of the fracture site, and attaching a second coupler to the element and to the bone on a second side of the fracture site. In this manner, the responsive zone is positioned adjacent the fracture site. In one aspect, the force applied to the elongate element to lengthen the responsive zone the desired amount corresponds to a desired compressive force to be applied to the fractured bone when the element is coupled thereto. Again, the shape memory material may be nitinol, or other shape memory materials compatible with the human body.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

BRIEF DESCRIPTION OF THE DRAWINGS

FIG. 1A is an overall view of a dynamic compression bone screw according to an embodiment of the present invention;

FIGS. 1B and 1C are simplified views of steps for forming the dynamic compression bone screw depicted in FIG. 1A;

FIGS. 2A-2C schematically depict the use of the dynamic compression bone screw of FIG. 1A for repairing a bone fracture;

FIG. 5A is an overall view of the bone fixation device shown in FIG. 4;

FIGS. 5B-5I are additional views of the fixation device shown in FIG. 5A, including a bottom view (FIG. 5A), a top view (FIG. 5B), a longitudinal cross-sectional view (FIG. 5C), a close-up bottom view of an expansive zone (FIG. 5D), an end view (FIG. 5E) and a side view (FIG. 5F);

DETAILED DESCRIPTION OF THE INVENTION

Figure 3F:
FIG. 3F is an overall view of the bone screw depicted in FIG. 3A.
Figure 3D:
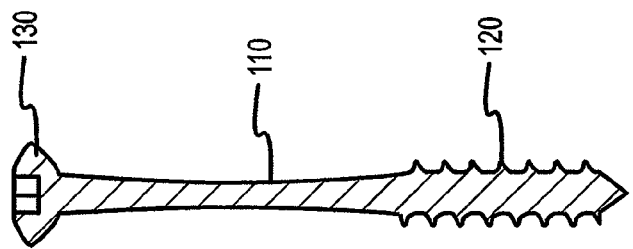
FIG. 3D is a longitudinal cross-sectional view of the bone screw depicted in FIG. 3A.
Figure 3B:
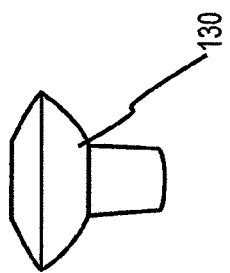
FIGS. 3B and 3C are close-up views of the screw head and threaded portion, respectively, for the bone screw depicted in FIG. 3A.
Figure 3C:
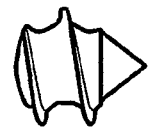
Figure 3A:
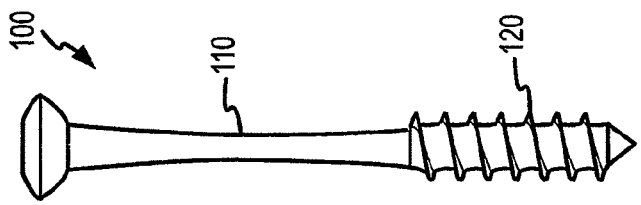
FIG. 3A is a side view of the dynamic compression bone screw of FIG. 1A.
Figure 3E:
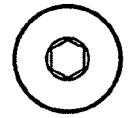
FIG. 3E is a top view of the bone screw depicted in FIG. 3A.

It has been determined that when a bone is set and a compressive force is applied to the fracture fixation device, the force between the fragments ends decreases rapidly as a function of time. Ideally, the fixation device is able to maintain a compressive force, which will allow for the continuation of healing through reduction of the fracture gap, and stability of the fracture gap. If this does not occur, a loss of compression may be followed by the lack of union and stability of the fracture site, which in turn reduces the healing. A fracture fixation device is put in place to stabilize the fracture site, however, if the compressive force is not present then micromotion between the fracture ends may occur. This, in turn, may cause unnecessary resorption, which will lead to nonunion of the bone or the presence of large voids. These reasons show the importance of a device to actively match the changes in the body, as well as have a similar response as bone.

Embodiments of the present invention include bone fixation devices, including plates, bone nails such as intramedullary nails, bone screws, and the like, that can provide sustained compression (spontaneous dynamic compression) across a bone fracture over time. The dynamic compressive forces are stable or generally stable as a function of bone surface resorption at the fracture site, facilitating improved bone healing and reducing non-union rates. Some bone fixation devices of the present invention will allow for approximately six percent (6%) relaxation before compressive force loss. In contrast, typical stainless steel or titanium bone screws lose their compressive forces after about one percent (1%) resorption at the fracture surface.

FIGS. 1A-2C depict a dynamic compression bone screw 100 according to an embodiment of the present invention. Bone screw 100 shown in FIG. 1A is further described in conjunction with FIGS. 3A-3F. In a particular embodiment, bone screw 100 is formed from nickel titanium, a shape memory alloy referred to as Nitinol. As shown in FIGS. 1B and 1C, screw 100 is formed from a Nitinol stock or block, and may be heat treated to produce desired characteristics. Shape memory alloys, such as Nitinol, exhibit the capacity to recover relatively large strains (e.g., about 6%) by the application of heat (shape memory) or by gradual unloading (pseudo-elasticity). The present invention exploits the large strain capacity and recovery behavior of shape memory alloys such as Nitinol for bone repair with novel devices, systems, and methods. In one embodiment, the fixation devices, such as screw 100, are machined from a shape memory material such as Nitinol that is thermally treated to exhibit pseudo-elasticity at body temperature. The overall screw geometry, responsive element geometry, and material heat treatment will be specified to sustain the necessary compressive forces as a function of fracture site conditions.

The shape memory effect of Nitinol is the temperature-induced transformation between the malleable martensite (lower temperature) phase and the more rigid austenite phase (higher temperature) that exhibits the desired pre-set shape. Exploitation of the thermally driven phase change helps some embodiments of the present invention deliver desired bone fixation results. Superelastic effect of Nitinol refers to the return to its pre-set austenite configuration upon unloading after elastic deformation. The initiation of superelastic behavior of Nitinol requires the formation of stress induced martensite (SIM) from the austenite phase, such as by the application of an external load or stress. Reduction of the external load or stress induces formation of the austenite phase and hence its pre-set configuration. SIM Nitinol is able to accumulate large deflection (strain) at a nearly constant load (stress). The relatively flat region of the Nitinol load-to-deflection relationship can be used for some devices of the present invention.

Figure 9A:
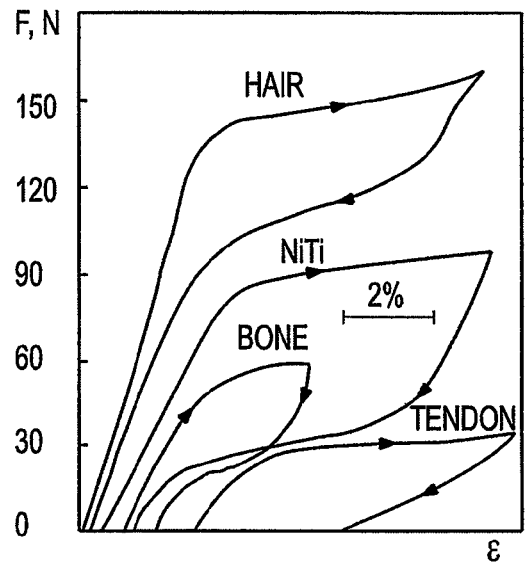
FIGS. 9A and 9B are graphical views of material properties of bone fixation screws and devices according to an embodiment of the present invention.

Some embodiments of the present invention take advantage of the stress/strain (modulus) of NiTi, depicted in FIG. 9A. Such characteristics of NiTi are beneficial in the development and use of improved total joint implants, for example. This property of NiTi decreases overall bone to implant interface stresses, resulting in a longer implant lifetime. Embodiments of the present invention, particularly those using NiTi, help the bone maintain load, which increases healing and helps smaller implants to maintain the same or similar stability as larger ones in similar areas of fixation by reducing stress/strain and sheering forces.

Formation of SIM phase within a responsive zone of screw 100, or other osteosynthetic implants and devices, may be achieved prior to surgical placement or as a result of surgical placement. For the bone screws 100 depicted in FIG. 1A, the responsive zone of screw will be designed to initiate SIM formation as a result of the installation process. This occurs, at least in part, due to the elongating forces applied to the screw when the screw is used. Additional details on the responsive zone are discussed in conjunction with FIGS. 3A-3F.

One technique for fracture fixation is the placement of a lag screw across the appositional ends of a break in the bony cortex. Inserting the screw across the fracture site helps generate the dynamic force capacity in the screw. As shown in FIG. 2A, bone screw 100 is inserted at an angle relative to a fracture site 210. Screw 100 is rotated to draw the two bone fragments 220 towards one another, creating a compressive force therebetween. The rotational torque used to turn screw 100 is translated into axial compression between bone fragments 220. The result is the proper alignment of bone fragments 220 as shown in FIG. 2B. Screw 100 maintains a compressive force on bone fragments 220 for a much longer period of time than traditional bone screws formed of steel, titanium, or the like. As a result, a more fully healed fracture site 210 results (FIG. 2C). During healing and bone absorption, the force generated by prior-art screws can decrease leaving a less compressive force acting across the fracture site 210 over time. In contrast, bone screws 100 of the present invention are a dynamic screw that can maintain higher compression values over a longer course of healing. Advantages of screw 100 includes better promotion of direct bone healing, reduction in non-union rates in high risk fracture sites, and a reduction in bone implant site resorption. In some embodiments, at least some of these advantages are achieved by the use of a shape memory material, such as Nitinol, and its inherently similar stress/strain properties to those of bone.

FIGS. 3A-3F depict further details on bone screw 100 according to an embodiment of the present invention. It will be appreciated by those skilled in the art that FIGS. 3A-3F depict a particular example, and the present invention is not limited to the dimensions and configurations shown therein. As can best be seen in FIGS. 3A, 3D, and 3F, bone screw 100 has a shank portion 110 with a diminished thickness or radius compared to the radius or thickness of a threaded portion 120 or of a head 130. In this manner, the reduced area of shank portion 110 allows for a stress concentration to be localized over shank portion 110, which allows shank portion 110 to elongate to form a responsive element or zone. In one embodiment, the elongation of shank portion 110 occurs during the insertion process into the fractured bone, as depicted in FIG. 2B. By using the responsive element or shank portion 110, bone screw 100 is able to localize the force caused by the SIM over the fracture site. The non-responsive screw portions, such as head 130, stays generally strain-free and contributes little force to the bone due to SIM.

Figure 3G:
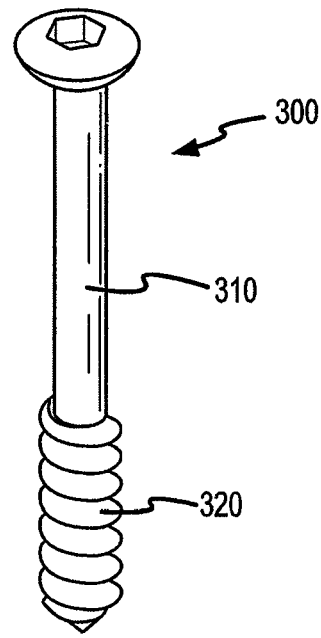
FIG. 3G is an overall view of a dynamic compression bone screw according to an alternative embodiment of the present invention.

In an alternative embodiment, a bone screw 300 depicted in FIG. 3G has a generally uniform diameter through a shank portion 310. In this embodiment, only shank portion 310 is formed of a shape memory material, with threaded end portion 320 comprising a stiffer region less susceptible to elongation.

Figure 4:
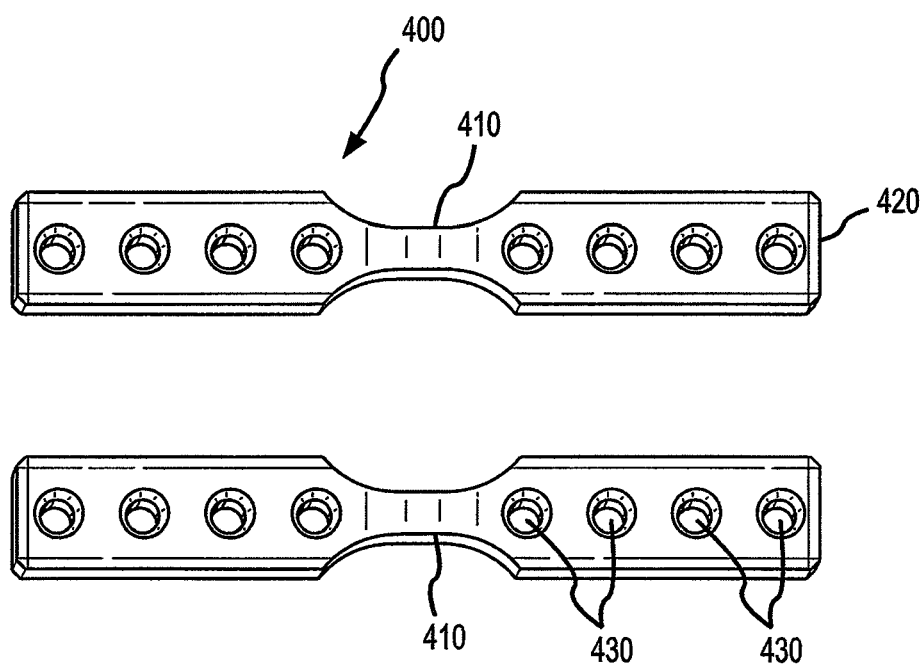
FIG. 4 is an overall view of two bone fixation devices according to an embodiment of the present invention.

Turning now to FIG. 4, a bone fixation device 400 according to an embodiment of the present invention will be described. Bone fixation device 400 allows for a longer and greater sustained compressive force. For example, current bone plates applied to a fractured surface tend to lose compressive force within two days to two weeks after surgery, thus slowing the healing process. Additional problems with prior-art plates, such as deflections and rigidity, also result in a greater chance of refracture and slow healing. In one embodiment of the present invention, bone fixation device 400 comprises a shape memory alloy, that may be Nitinol or the like. Fixation device 400 is a dynamic device that can change over time with the human body into which it is inserted. In a preferred embodiment, device 400 comprises Nitinol, due in part to its capacity to recover large strains over time. In one embodiment, this is accomplished through the creation of device 400 having a responsive zone section 410. In some embodiments, responsive zone 410 has a smaller overall cross-sectional area than the non-responsive zone(s) of device 400. Responsive zone 410 is used to localize the elongation of device 400 to that area. In one embodiment, device 400 is elongated based on the application of a force similar to or the same as the force required to stabilize the fracture to which device 400 is applied. Device 400 will be elongated based on the force required to stabilize the fracture and apply the necessary healing force. After device 400 has been elongated, in one embodiment it is held in an elongated state by an external clamp or similar structure to prevent recovery motion of device 400. After device 400 is affixed to the fracture site, the clamp, or other retaining mechanism can be removed. Further details on the use of device 400 are discussed in conjunction with FIGS. 7A and 7B.

FIGS. 5A-5I depict various views of device 400 or portions of device 400, according to particular embodiments of the present invention. Again, the dimensions, including the lengths, widths, thicknesses and radii of curvature, may vary within the scope of the present invention from those shown in the figures. More specifically, the figures include a longitudinal cross-sectional view (FIG. 5C), a top view (FIG. 5B), a bottom view (FIG. 5A), a side view (FIG. 5F), an end view (FIG. 5E), and a close-up bottom view of expansive zone 410 (FIG. 5D), of device 400. In a preferred embodiment, device 400 is coupled to a bone having a fracture site so that responsive zone 410 is disposed adjacent the fracture site. This arrangement can be seen in FIGS. 6A and 6B.

Figure 6A:
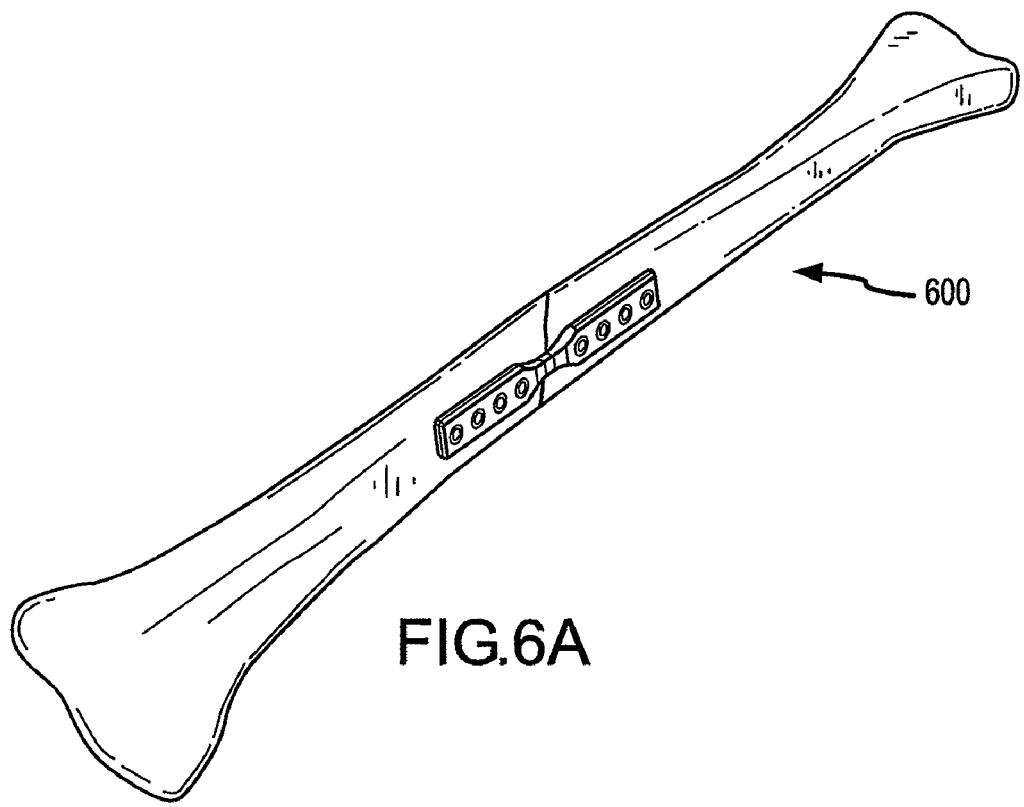
FIGS. 6A and 6B are overall views of a fixation device coupled to a bone having a fracture site.
Figure 6B:
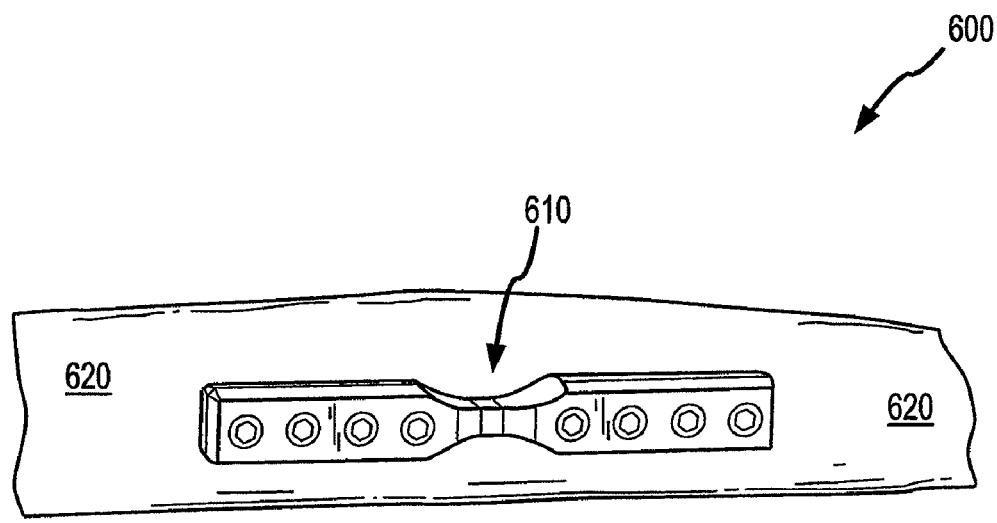

As shown, device 400 has one or more holes 430 disposed on each side of responsive zone 410 so that device 400 may be coupled to a fractured bone 600. While FIGS. 6A and 6B depict four holes 430 on each side of the fracture site, a greater or lesser number of holes 430 may be used within the scope of the present invention. In some embodiments, holes 430 are adapted to receive a screw or other fixation element to affix device 400 to bone 600. The coupling of device 400 to bone 600 preferably positions responsive zone 410 across or adjacent a bone fracture site 610. This may involve attaching one end of device 400 to one bone segment 620 and the second end of device 400 to the opposing bone segment 620. In some embodiments, the screw or fixation element used to couple device 400 to bone segment 620 comprises a bone screw, which may be made of stainless steel, titanium or the like. In a particular embodiment, screws or fixation elements used to coupled device 400 to bone 600 comprise a shape memory alloy, such as Nitinol.

Figure 7A:
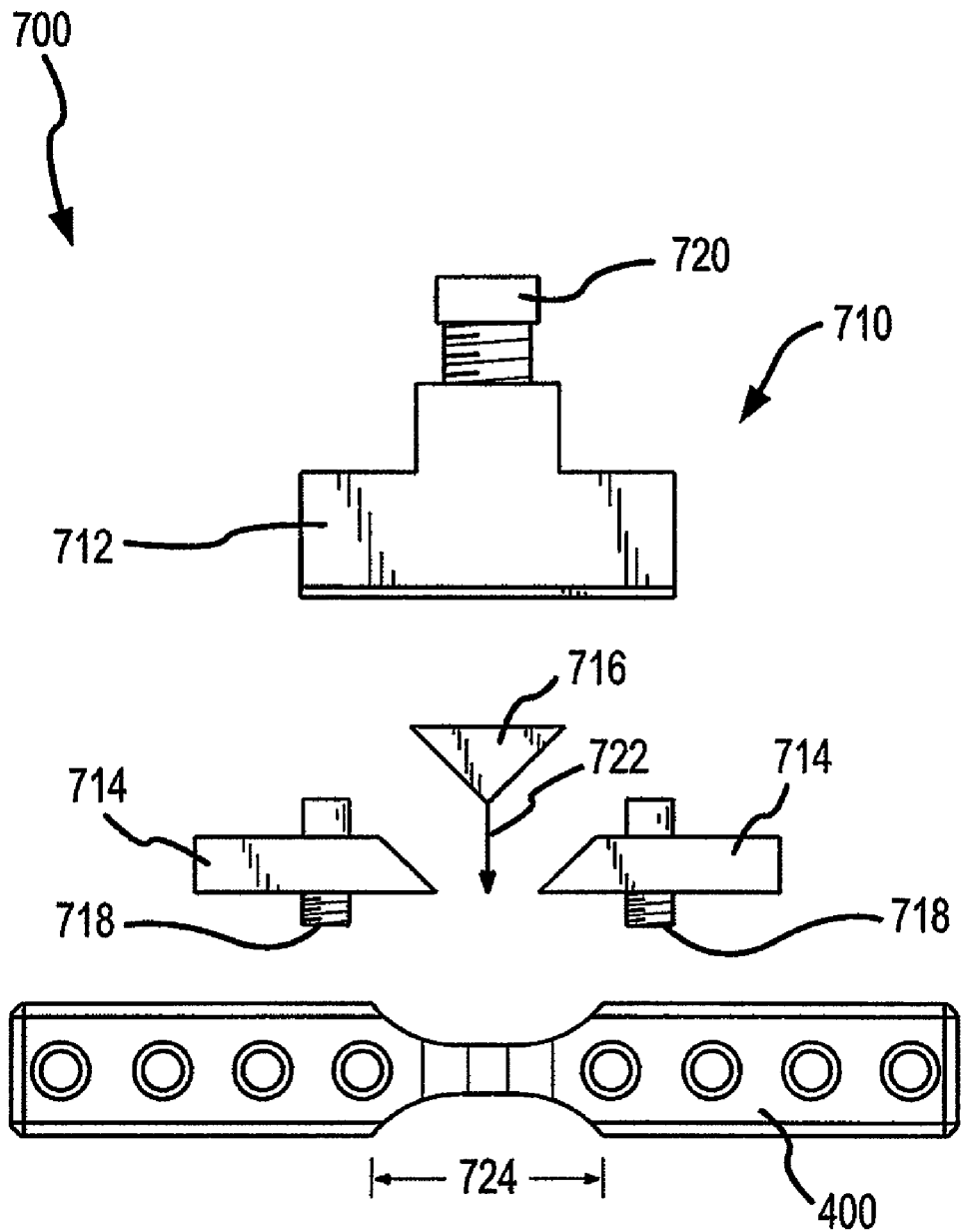
FIGS. 7A and 7B are exploded and assembled overall views, respectively, of a bone fixation system according to an embodiment of the present invention using the fixation device shown in FIG. 4.
Figure 7B:
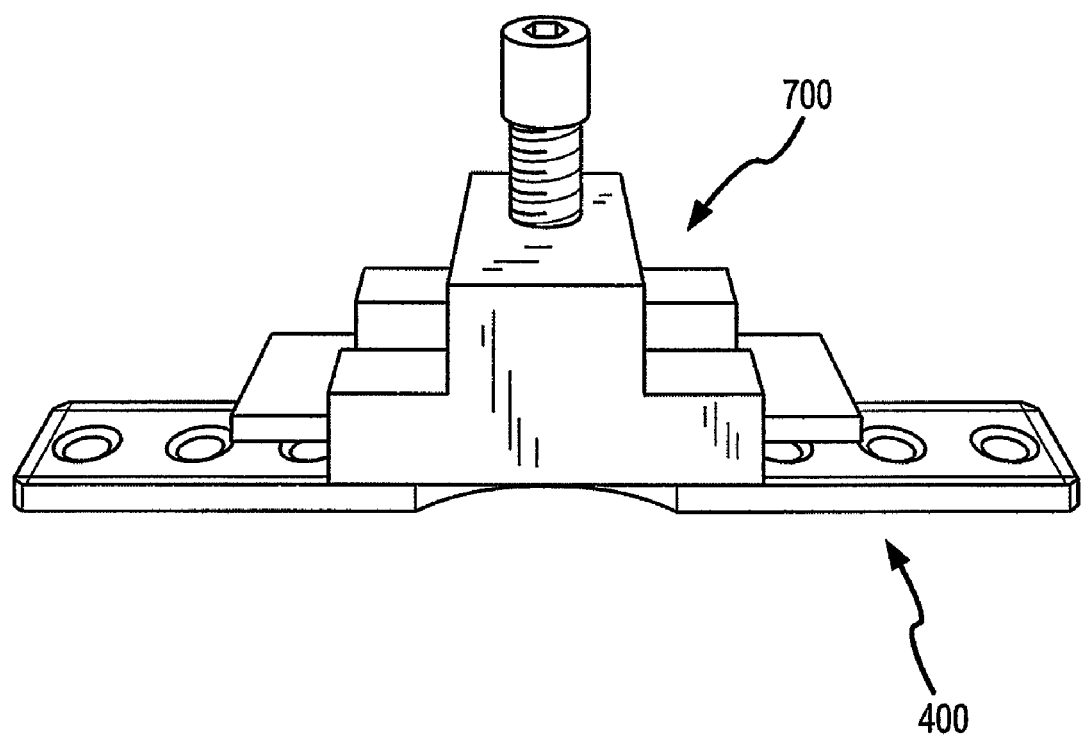

FIGS. 7A and 7B depict a bone fixation system 700 according to an embodiment of the present invention. System 700 includes fixation device 400 as previously described, and a clamp 710. While FIG. 7A depicts a single example of clamp 710, other clamp types fall within the scope of the present invention. Further, alternative devices may be used in lieu of clamp 710, provided the alternative devices are capable of attaching to device 400, and preferably are capable of holding device 400 in a desired position or elongated state. In operation, an elongating force is applied to device 400 to stretch or elongate device 400 to a prescribed length. As described further below, the application of the prescribed force is determined at least in part by the necessary force to provide healing effect to the bone to which device 400 will be applied. Once device 400 is elongated to the desired length, clamp 710 is used to maintain device 400 in the elongated position. Clamp 710 maintains the elongated position of device 400 until device 400 is attached to the fractured bone. Once device 400 is attached to the fractured bone, clamp 710 may be removed from device 400. In this manner, device 400 is attached to the fractured site and, upon the release of clamp 710, device 400 provides the desired compressive force through the fractured location. Again, in some embodiments device 400 comprises a shape memory material, and in a particular embodiment comprises Nitinol. Preferably, the application of the compressive force is of sufficient duration to facilitate healing as well as to avoid some or all of the other problems associated with prior-art devices constructed of stainless steel, titanium, or similar materials.

In the depicted embodiment, clamp 710 comprises a main component 712, first and second device-engaging components 714, and a wedge element 716. In one embodiment, device-engaging components 714 are disposed so that screws, lugs, posts or the like 718 extending from components 714 pass at least partially through corresponding holes 430 in device 400. Main component 712 is then coupled to device-engaging components 714 with wedge element 716 positioned therebetween. By rotating or depressing a pressure applicator 720, which in one embodiment is a screw, a force is applied to wedge 716. The application of a force to wedge 716 in the direction shown by arrow 722 causes an outward force to be applied to components 714, as shown by arrows 724. As can be seen in FIG. 7A, the force depicted by arrows 724 results in an elongating force being applied to device 400 through the use of screws, lugs, or posts 718. By controlling the physical relationship between pressure applicator 720 and components 714, the elongating force to device 400 may be controlled. The coupled configuration of clamp 700 with device 400 is generally depicted in FIG. 7B.

In another embodiment, a separate device or system is used to apply the elongating force to device 400. This may occur, for example, by pulling on opposing ends of device 400 to create an elongating force similar to that represented by arrows 724. Once device 400 has been elongated the desired amount, clamp 710 may be coupled to device 400 in the manner substantially as described above to hold device 400 in the elongated position. In this embodiment, pressure applicator 720 is operated so that the screws, lugs, or posts 718 engage holes 430 to hold device 400 in its desired elongated state. Again, device 400 is then coupled to bone 600, which preferably positions responsive zone 410 across or adjacent bone fracture site 610. This may involve attaching one end of device 400 to one bone segment 620 and the second end of device 400 to the opposing bone segment 620. Once device 400 is coupled to bone 600, clamp 700 is removed.

The present invention further provides bone fixation rods, nails and the like. In one embodiment, a bone fixation rod or nail 800 has a first end 810 and a second end 812, with a middle section 814 disposed therebetween. In one embodiment, some or all of rod 800 comprises a shape memory alloy, that in a preferred embodiment comprises Nitinol. For example, in one embodiment, middle section 814 comprises Nitinol. In this manner, middle section 814 is a responsive zone having the characteristics as generally described herein. In another embodiment, one or both of first end 810 and second end 812 comprise Nitinol. In still another embodiment, the entire rod 800 is Nitinol.

In one embodiment, rod 800 is a dynamic intramedullary nail. Such a device may be used, for example, in retrograde tibio-talo-calcaneal fusions. Nail 800 addresses fracture site compression problems, as described generally herein in conjunction with prior embodiments, as well as vascular preservation issues. For example, rod 800 may provide dynamic compression across a fusion site in a manner which allows for the use of smaller rods 800, or nails. By having a smaller diameter rod or nail 800 compared to prior art nails of titanium or the like, this would aid in preserving the medullary blood supply.

Figure 8:
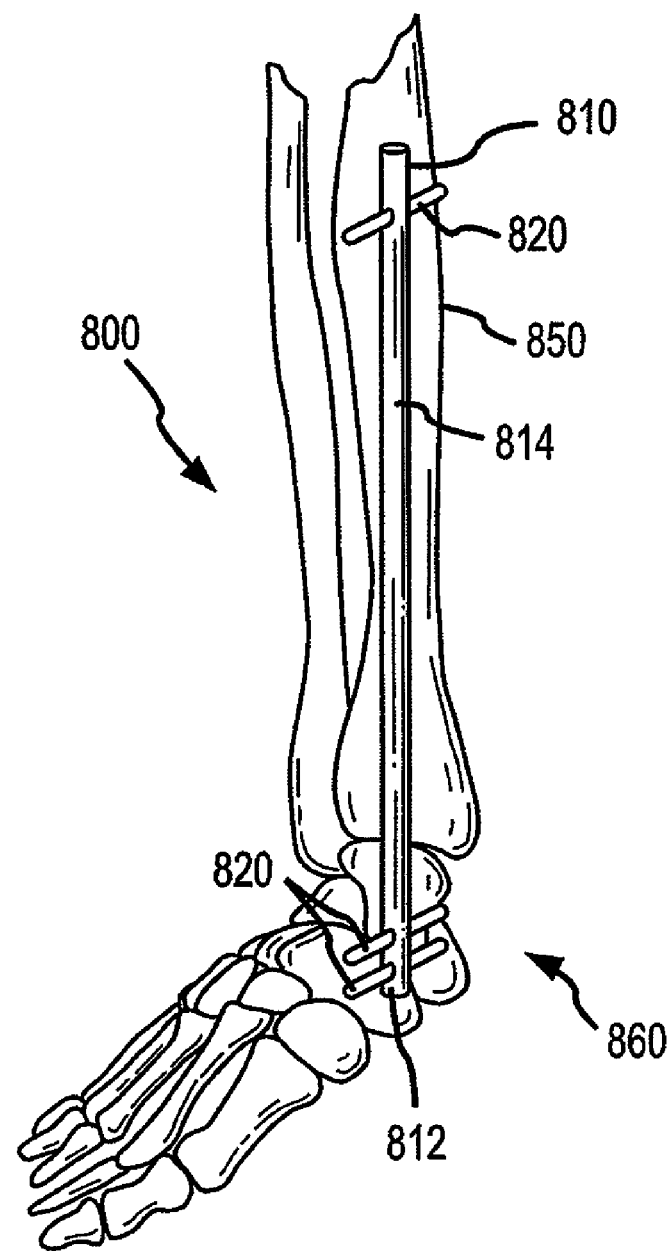
FIG. 8 is an overall view of a bone fixation device according to an alternative embodiment of the present invention.

As shown in FIG. 8, rod or nail 800 is inserted into a bone 850. Rod 800 insertion occurs, in one embodiment, by reaming the bone's medullary canal, and hammering or otherwise driving nail 800 into place. Nail 800 then may be locked relative to the bone with one or more interference or locking screws 820. While the embodiment shown in FIG. 8 depicts a single screw 820 near end 810 and two screws 820 near end 812, it will be appreciated by those skilled in the art that the number of screws 820 may vary within the scope of the present invention. Further, the interference or locking screws 820 may comprise nails, pins or the like. The dimensions of rod 800 and screws 820, including the lengths, widths, diameters, and thicknesses, may vary within the scope of the present invention and may determined, at least in part, by the particular bone(s) and/or joint(s) into which the device is being inserted or otherwise coupled.

In some embodiments, nail or rod 800 is designed to allow for the release of the responsive element or zone portion thereof, allowing the rod or nail 800 to shorten. This is accomplished, at least in part, by having the responsive zone of rod 800 comprise a shape memory alloy such as Nitinol as described above in conjunction with screw 300. In this manner, the release of the responsive element-portion of nail 800 draws locking screws 820 on opposing sides of the responsive zone closer together. Dynamic compression on bone 850 results. In one embodiment, the responsive zone, which may include ends 810, 812 and/or middle section 814, is positioned at a desired location(s) within bone 850 or joint 860 to facilitate bone healing. For example, the responsive zone may be positioned adjacent or spanning a fracture site within bone 850, may be positioned within a joint 860, or at other locations at which increased and/or sustained dynamic pressure is desired.

Bone fixation devices of the present invention, including nails 800, screws 300 and plates 400, may be inserted with one or more sets of instrumentation that also are included within the scope of the present invention. For example, the instrumentation for implantation may be comprised of screws and plates, hammers or other compression devices, clamps or other holding devices, torsion devices such as screwdrivers, torque wrenches or the like for inserting screws, rods and plates. In one embodiment, a torque wrench is provided having a preloaded setting that allows the surgeon to determine whether the screw 300 pseudo elasticity has been activated upon insertion at the fracture site.

Figure 9B:
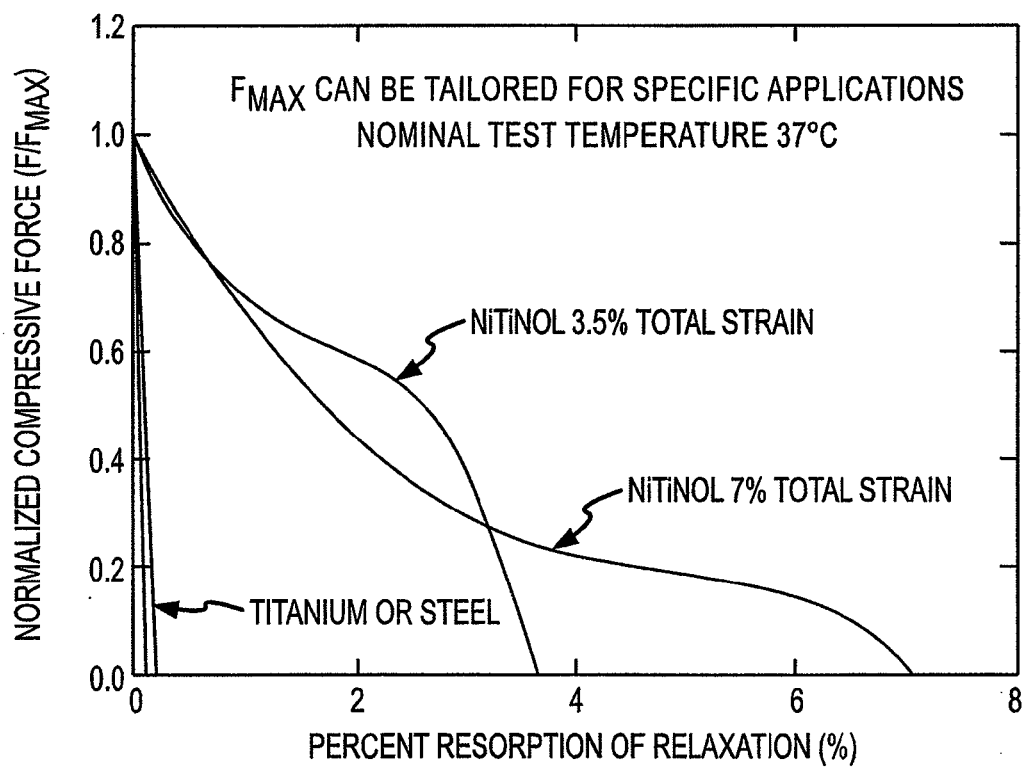

FIG. 9A depicts the stress-strain diagram for living tissues and a nickel titanium alloy. Nickel titanium, and in particular Nitinol, exhibits desirable strain recovery characteristics. The temperature at which Nitinol recovers is known as the transformation temperature ($T_t$). The transformation temperature may be determined using various heat treatments on the material. The material then may demonstrate pseudo elastic (PE) and shape memory (SM) properties, depending at least in part on the relationship between $T_t$ and the surrounding temperature $T_a$ (e.g., atmospheric temperature, internal body temperature, or the like). The PE state is observed when $T_a$ is greater than $T_t$. When the material is stretched from an applied force, a permanent strain is observed. When the force is removed, the material recovers the strain. The SM state occurs when $T_t$ is greater than $T_a$. The material is deformed at above $T_a$, and remains deformed until a temperature is applied which is above $T_t$. These characteristics are useful for fashioning fixation devices according to some embodiments of the present invention. FIG. 9B depicts the inventors experimental results showing the affect of total strain on the unloading profile of SIM Nitinol.

The force that the physician wants to place over fracture site 210 or 610 with screw 100, nail 800, plate 400 or other fixation devices within the scope of the present invention can be defined as $F_R$. The physician also can determine the anticipated change in length ($\Delta L$) of relaxation/resorption needed to maintain the stability in the fracture. This may involve determining the distant or amount the bone and/or surrounding tissues will relax during the healing period. From this information the cross sectional area and length of a bone fixation device, such as screw 100, nail 800 and/or device 400 can be calculated, respectively.

Figure 10A:
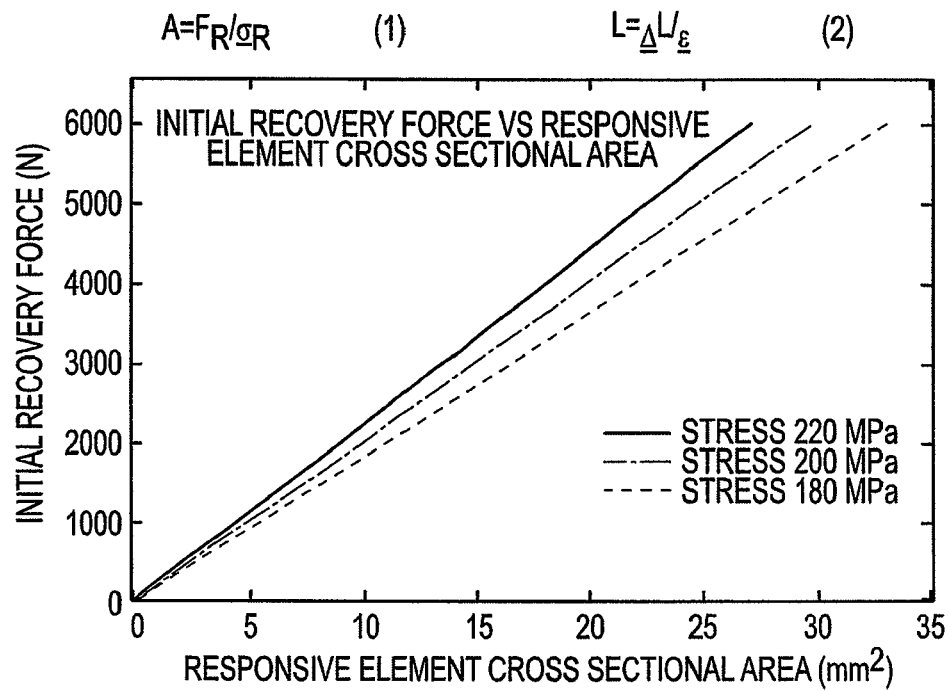
FIGS. 10A and 10B are graphical depictions of characteristics of bone screws and fixation devices according to embodiments of the present invention.

Using equation (1) below, the cross sectional area can be calculated. Using equation (2) below, the total length of the responsive element can be calculated. In these equations, A is the cross-sectional area, $F_R$ is the physician-specified recovery force, $\sigma_R$ is the tensile recovery stress (a material property), L is the length of the responsive zone or element, $\Delta L$ is the physician-specified change in length of the responsive zone or element, and $\epsilon$ is the tensile strain (a material property). The total length and cross sectional area are used for the manufacturing of the plate or screw in order to meet the physician's needs. FIGS. 10A and 0B show an example of possible areas and length, that can be determined by the physician.

$$A = F_R/\sigma_R \quad (1)$$

$$L = \Delta L/\epsilon \quad (2)$$

The responsive element or responsive zone, in a preferred embodiment, has a smaller cross sectional area than the non-responsive part. This reduction of the area allows for the stress concentration to be localized over the element or zone, which in turn elongates only the responsive element or zone. By using the responsive element or zone, the application is able to localize the force caused by the Stress Induced Martensite (SIM) over the fracture, while the non-responsive element stays generally strain free and contributes minimal forces to the bone due to SIM.

Several devices and systems of the present invention are developed from a Shape Memory Alloy (SMA) to actively respond to the changes of the human body, especially in the bone response. In some embodiments, the inventors studied and used the SMA nickel titanium, or Nitinol. NiTiNOL is biologically compatible with the endoskeleton structure, as well as being strong and durable. Several embodiments of the present invention harness the material characteristics of NiTiNOL.

The below discussion covers the steps to manufacture a dynamic compression bone screw, nail, bone fixation device or plate, and other active devices from NiTiNOL, and the machining of NiTiNOL devices. A brief description of the heat treating, composition and deformation techniques used will be addressed. It will be appreciated by those skilled in the art that the manufacturing techniques described represent just some of the embodiments of the present invention.

Material Preprocesses

Figure 10B:
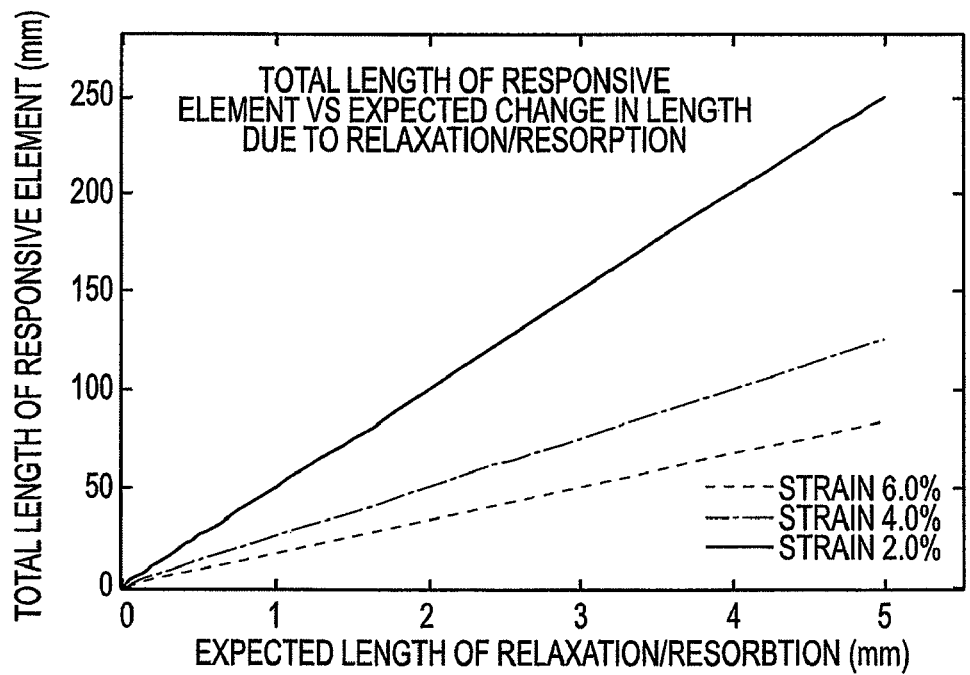

It is desirable to develop an accurate stress strain response for various states of the NiTiNOL. Below are the steps used to characterize a particular composition of an SMA of NiTiNOL according to an embodiment of the present invention:

1. Bars of Hot Rolled Ti-50.9% at % Ni, and Cold Drawn Ti-50.9% at. % Ni. were obtained from Special Metals.
2. The materials are cut into desired bone plate, nail and screw shapes from the bars using Electro Discharge Machining (EDM). This process allowed for the presence of mechanical work to be minimal in the samples. The specimens were cut into dog bone samples for tension and rectangular blocks for compression. All tests are run in monotonic strain control.
3. Various heat treatments were applied to the Hot Rolled Material, based on the use of $Ti_3Ni_4$ precipitants to move the Martensite start ($M_s$) and finish ($M_f$) temperatures, as well as the Austenite start ($A_s$) and finish temperatures ($A_f$). The results were determined through the transformation peaks being observed using a Differential Scanning calorimeter.
4. The various stress-strain responses were examined with regard to heat treatment. This allows for certain characteristics to be harnessed in the design. The uses of various heat treatments allow for the stress recovery and strain recovery to be changed.
5. Using the material response in its loaded condition, a cross sectional area is designed as briefly discussed in conjunction with FIGS. 10A-10B.

Bone Screw/Nail

Some embodiments of bone fixation devices of the present invention are developed to actively adapt to the resorption across the fracture site. One such bone screw manufacturing process according to the present invention is provided below.

The manufacture of other fixation devices within the scope of the present invention follow a similar or same process.

1. Using the manufacturing results 1-5 above, the actual design of the responsive element or responsive zone can be determined. The specific calculations of the responsive element for the bone screw are discussed briefly in conjunction with FIGS. 10A-10B, and in more detail in Provisional Application No. 60/563,952, previously incorporated herein by reference.
2. The bars of NiTiNOL are sent to be EDM into smaller cylindrical sections. At this time, no heat treatment has been applied and the material is said to be in its as-received state.
3. The smaller cylinders are heat treated for about 600° C. for about 30 minutes, which in turn reduces the hardness and places the material in a state more susceptible to machining.
4. The screw is machined, such as on a lathe, at a cutting speed similar to stainless steel (e.g., about 300 RPMs). Concurrently, the NiTiNOL is flooded with cutting fluid to reduce the work hardening effects of the cutting surface.
5. After machining, the final part is heat treated to the appropriate temperature based on the material characterization and design phase, listed above. In a particular embodiment, the heat treatment related to the material composition of 50.9 is about 350° C. for about 1.5 hours.
6. The screw is autoclaved and deployed. The reactive element is stretched using the principle of the screws head and threads.

Bone Fixation Device or Plate

Use of a bone fixation device or a bone plate may be necessary to add a large area of stabilization over the fracture site. The device or plate may be used in unison with a bone screw. The bone fixation device or plate actively adapts to the resorption of a fracture site and compensates for the resorption located at the head and threads of the screws. Below are the instructions used to develop a NiTiNOL bone plate according to an embodiment of the present invention.

1. Using the manufacturing results 1-5, the actual design of the responsive element can be determined. The specifics of the responsive element are discussed briefly in conjunction with FIGS. 10A-10B, and in more detail in Provisional Application No. 60/563,952, previously incorporated herein by reference.
2. Based on the type of fracture and amount of resorption expected, the final compressive force required for the plate to respond to the bone is designed using the stress/strain diagram.
3. The bars of the NiTiNOL are sent to be EDM into the final design of the plates. At this time, no heat treatment has been applied and the material is said to be in its as-received state.
   It is possible to use the above "softening" heat treatment to machine the plates on a mill. The smaller rectangles will be cut from the bar, and then heat treated at about 600° C. for about 30 minutes, which in turn reduces the hardness and places the material in a more "machining friendly" state.
4. The plate has its oxide layer left from the EDM mechanically removed.
5. Based on the results of the material characterization stage, the as-received bone plates are heat treated to get the desired properties. Similar to the screw, the heat treatment related to the material composition of 50.9 is about 350° C. for about 1.5 hours.
6. Once the application of the plate is known, it is stretched using an external device to a predetermined strain and held fixed in place with a brace.
7. The entire setup is then sterilized by autoclave and finally deployed over the fracture site.

Other NiTiNOL Devices Including a Responsive Element

Other devices can benefit from the use of NiTiNOL or other SMA in an active responsive element. For example an interlocking bone marrow nail can be formed. The design of the nail is similar to the screw, and encompasses a similar responsive element. The design comes from the characterization of the NiTiNOL as discussed herein. Still other devices that could incorporate the responsive element include an artificial disk replacement used in a patient's vertebra. The responsive element could be designed to allow different forces between particular vertebrae. For example, a person with a large upper torso has different stress contribution between the upper vertebrae and lower vertebrae, than a person with a smaller torso. Other uses of SMAs such as Nitinol also exist for creating actively responsive elements.

The invention has now been described in detail. However, it will be appreciated that the invention may be carried out in ways other than those illustrated in the aforesaid discussion, and that certain changes and modifications may be practiced within the scope of the appended claims. Accordingly, the scope of this invention is not intended to be limited by those specific examples, but rather is to be accorded the scope represented in the following claims.

What is claimed is:

1. A method, comprising:
   inserting a bone device having a longitudinal axis into a first bone fragment and a second bone fragment, wherein the inserting causes a first portion of the bone device to contact the first bone fragment and causes a second portion of the bone device to contact the second bone fragment, the second portion different from the first portion;
   wherein the bone device comprises a shape memory alloy having an austenite finish temperature;
   creating in a responsive portion of the bone device at least a partial transformation into a stress-induced martensitic phase via stretching the responsive portion along the longitudinal axis;
   after performing the stretching, fixing the second portion of the bone device to the second bone fragment; and
   wherein the creating is performed at a temperature greater than the austenite finish temperature of the shape memory alloy.

2. The method of claim 1, wherein stretching the bone device is performed with the bone device substantially in an austenitic phase.

3. The method of claim 1, further comprising:
   before performing the stretching, fixing the bone device to the first bone fragment.

4. The method of claim 3, further comprising:
   holding the responsive portion above the austenite finish temperature of the shape memory alloy while the fixing the bone device to the first bone fragment is performed.

5. The method of claim 1, further comprising:
   holding the shape memory alloy at a temperature greater than the austenite finish temperature of the shape memory alloy while the stretching is performed.

6. The method of claim 1, further comprising:
   holding the responsive portion above the austenite finish temperature of the shape memory alloy while the fixing the second portion is performed.

7. The method of claim 1, wherein inserting the bone device into the second bone fragment is performed while the responsive portion is substantially in an austenitic phase.

8. The method of claim 1, wherein inserting the bone device into the first bone fragment is performed while the responsive portion is substantially in an austenitic phase.

9. The method of claim 1, wherein the first portion comprises the shape memory alloy.

10. The method of claim 1, wherein the second portion comprises the shape memory alloy.

* * * * *